United States Patent
Subramanyam et al.

(10) Patent No.: US 6,375,933 B1
(45) Date of Patent: Apr. 23, 2002

(54) DUAL COMPONENT DENTIFRICE FOR REDUCING MOUTH ODORS

(75) Inventors: Ravi Subramanyam, Belle Mead; Malcolm Williams; Petros Gebreselassie, both of Piscataway; Xiaoyan Liu, Highland Park; Angelo Zaccagnino, Milltown; James G. Masters, Ringoes, all of NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 09/753,854

(22) Filed: Jan. 3, 2001

(51) Int. Cl.[7] ............................. A61K 7/16; A61K 7/20
(52) U.S. Cl. ............................................ 424/49; 424/53
(58) Field of Search ............................................ 424/49–58

(56) References Cited

U.S. PATENT DOCUMENTS 4,902,498 A * 2/1990 Agricola et al. .............. 424/52
5,281,412 A * 1/1994 Lukacovic et al. ........... 424/52
5,616,313 A * 4/1997 Williams et al. .............. 424/49
6,132,702 A * 10/2000 Witt et al. ..................... 424/53

FOREIGN PATENT DOCUMENTS

| DE | 19854349 | * | 5/2000 |
| GB | 2 289841 | * | 12/1995 |
| WO | 98/17195 | * | 4/1998 |

* cited by examiner

Primary Examiner—Shep K. Rose
(74) Attorney, Agent, or Firm—Paul Shapiro

(57) ABSTRACT

A dual component oral composition to suppress oral malodor and provide long lasting breath protection in the oral cavity which comprises a first dentifrice component having a substantially neutral pH and containing a zinc ion releasable compound and a chlorite ion releasable compound, the second dentifrice component having an acid pH, the first and second components being maintained separate from each other until dispensed and combined for application to teeth, the combined components having a pH of no greater than 7.

16 Claims, No Drawings

DUAL COMPONENT DENTIFRICE FOR REDUCING MOUTH ODORS

BACKGROUND OF THE INVENTION

1. Field of the Invention

The present invention relates to a dentifrice composition useful for reducing oral malodor, and more particularly to a dual component dental composition containing zinc and chlorite ion releasable compounds.

2. The Prior Art

"Oral composition" means a composition for topical applications to the oral cavity to clean and care for the teeth as well as the oral cavity surfaces. Representative of such compositions are oral hygiene products for delivering therapeutic and cosmetic benefits to the oral cavity such as mouthwashes or rinses, toothpaste, dental gels, tooth powder, chewing gum, lozenges, strips and similar products. The benefits delivered by oral compositions include the suppression of dental calculus formation and the prevention of dental disorders such as caries, periodontitis and gingivitis as well as the elimination of halitosis.

Dental plaque is a deposit which forms on teeth and consists of inorganic and organic components derived from saliva, food and bacteria which are present in the oral cavity. When plaque undergoes calcification it forms dental calculus composed largely of calcium and orthophosphate arranged in a crystal lattice called hydroxyapatite.

Oral malodor, clinically referred to as halitosis, is caused by the putrefactive activity of microorganisms on appropriate substrate components of dental plaque, debris adhering to mucous membranes and salivary cellular elements to produce volatile sulfur compounds primarily hydrogen sulfide, methyl mercaptan and traces of methyl sulfide.

Methods of inhibiting volatile sulfur compounds to reduce the production of mouth odor have included the use of oral compositions such as toothpastes and mouthrinses containing chlorite ions or zinc ions have been disclosed by the prior art, as for example, U.S. Pat. No. 6,132,702. U.S. Pat. No. 4,992,259. U.S. Pat. No. 5,753,217 discloses a method of reducing oral malodor comprising preparing a solution of sodium chlorite and a zinc salt and applying the solution as a mouth rinse, wherein the sodium chlorite concentration in the solution is between 500 and 1000 parts per million (ppm) and wherein the concentration of Zn ion in the solution is between 200 and 500.

Although useful as anti-malodor agents, applicants assays of the efficacy of chlorite ion releasable compounds as well as zinc ion releasable compounds have indicated that such compounds are not fully effective in suppressing oral malodor, and that efficacy improvements are necessary for full acceptance by consumers of oral care products containing these agents.

SUMMARY OF THE INVENTION

In accordance with the present invention there is provided a method to suppress oral malodor to provide long lasting breath protection wherein there is applied to the oral cavity a multicomponent dentifrice comprised of two separately housed, semi-solid aqueous components; the first component containing a zinc salt as the source of zinc ions and a chlorite salt as a source of chlorite ions in an orally acceptable vehicle having a substantially neutral pH of about 6.0 to 7.5 and the second component having an acid pH of from about 2.0 to about 6.0, whereby upon mixing and combination of the two components the pH of the final dentifrice is no greater than 6.5 with the generation of chlorine dioxide whereby there is effected an unexpected reduction in breath volatile sulfur compounds (VSC) responsible for breath malodor.

DESCRIPTION OF THE PREFERRED EMBODIMENTS

In use, the components of the two component dentifrice of the present invention comprise a first substantially neutral pH dentifrice component, and a second acidic dentifrice component. The two components are preferably formulated with water, humectants, surfactant and abrasive to have similar physical characteristics, so that the two components may be simultaneously delivered in desired predetermined amounts by extrusion when separately housed in a multi-compartmented container such as a tube or pump device.

The neutral pH dentifrice component of the present invention, has a pH of about 6.0 to 7.5 and preferably about 6.8. The acidic dentifrice component is prepared using a similar vehicle to which an acid compound has been added to adjust the pH of such dentifrice component in the acid range of about 2.0 to about 6.0 and preferably about 4.0 to about 5.5. The pH of the final dentifrice after components are combined for use is no greater than 6.5 and preferably between about 5.8 and about 6.4.

The humectant used in the preparation of the dentifrice components is generally a mixture of humectants, such as glycerol, sorbitol and a polyethylene glycol of molecular weight in the range of 200 to 1000, but other mixtures of humectants and single humectants may also be employed. The humectant content is in the range about of 10% to about 80% by weight and preferably about 20 to about 50% by weight of the dentifrice component. The water content is in the range of about 10 to about 40% by weight and preferably about 20 to about 30% by weight.

Thickeners include organic and inorganic thickeners. Inorganic thickeners which may be included in the dentifrice components include amorphous silicas such as Zeodent 165 available from Huber Corporation, and Sylox 15 from W. R. Grace.

Organic thickeners of natural and synthetic gums and colloids may also be used to prepare the dentifrice components of the present invention. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic thickener may be incorporated in the dentifrice components of the present invention at a concentration of about 0.5 to about 5% by weight and preferably about 1 to about 3% by weight. The organic thickener may be incorporated in the compositions of the present invention at a concentration of about 0.1 to about 3% by weight and preferably about 0.4 to about 1.5% by weight.

Surfactants may be incorporated in the dentifrices to provide foaming properties. The surfactant material is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

The surfactant is generally present in the dentifrice component compositions of the present invention at a concentration of about 0.5 to about 10.0% by weight and preferably about 1.0 to about 5.0% by weight.

Abrasives may be incorporated in the dentifrice components of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, calcined alumina and bentonite.

The concentration of abrasive in the dentifrice component compositions of the present invention will normally be in the range of 2 to about 40% by weight and preferably 5 to 25% by weight.

Zinc ion releasable compounds useful in the practice of the present invention are generally water soluble zinc salts including zinc nitrate, zinc citrate, zinc chloride, zinc sulfate, zinc bicarbonate and zinc oxalate with zinc nitrate being preferred. The zinc salt is generally incorporated in the neutral pH dentifrice component at a concentration of about 0.25 to about 10% by weight and preferably about 0.5 to about 2% by weight.

Chlorite ion releasable compounds include alkali metal chlorites, alkaline earth metal chlorites, and any other transition metals, inner transition metal chlorites and/or polymeric salts. Water soluble chlorite salts are preferred. Examples of suitable metal chlorites include calcium chlorite, barium chlorite, magnesium chlorite, lithium chlorite, sodium chlorite and potassium chlorite. Sodium chlorite and potassium chlorite are preferred. Sodium chlorite is particularly preferred. Mixtures of two or more sources of chlorite may also be used. The chlorite ion releasable salt is generally incorporated in the neutral pH dentifrice component at a concentration of about 0.5 to abut 5% by weight and preferably about 0.1 to about 1% by weight.

The acidic dentifrice component of the dentifrice composition of the present invention, which is maintained physically separate from the neutral dentifrice component until mixing before use, contains an acid or mixture of acids, to acidulate and thereby activate the chlorite compound present in the neutral dentifrice component to release chlorine dioxide, when the two components are combined prior to use.

Acidic compounds which can be present in the acidic dentifrice component of the present invention include both mineral and organic acids, such as, sulfuric acid, hydrochloric acid, malic acid, alginic acid, citric acid, succinic acid, lactic acid, tartaric acid, potassium bitartrate, acid sodium citrate, phosphoric acid, and sodium acid phosphate. Acid phosphates are preferred, including phosphoric acid, or salts of phosphoric acid containing the $PO_4$ ion, as such acids or acid salts thereof, such as sodium phosphate monobasic, not only provide the necessary acidity, but also provide phosphate ions, to inhibit any tooth enamel demineralization which may occur with the application of the two component dentifrice to the teeth. The preferred acid, phosphoric acid, is commercially available as a liquid at 85% concentration. The acid is added to the dentifrice component in an amount to maintain the pH of the dentifrice at a pH of about 2.0 to about 6.0 and preferably about 4.0 to about 5.5 when the neutral and acidic dentifrice components of the present invention are combined, the pH of the combined compositions is between about 5.8 to about 6.4.

Fluoride providing salts having anticaries efficacy may also be incorporated in the dentifrice of the present invention and are characterized by their ability to release fluoride ions in water. It is preferable to employ a water soluble fluoride salt providing about 10–2,000 ppm of fluoride ion, and preferably about 1000–1500 ppm of fluoride ion. Among these materials are water soluble inorganic metal salts, for example, sodium fluoride, potassium fluoride, sodium monofluorophosphate, stannous fluoride and sodium fluorosilicate. Sodium fluoride, sodium monoflurophosphate and stannous fluoride are preferred fluoride providing salts.

Pyrophosphate salts having anticalculus efficacy useful in the practice of the present invention include water soluble salts such as dialkali or tetraalkali metal pyrophosphate salts such as $Na_4P_2O_7$(TSPP), $K_4P_2O_7$, $Na_2K_2P_2O_7$, $Na_2H_2P_2O_7$ and $K_2H_2P_2O_7$. Polyphosphate salts may include the water soluble alkali metal tripolyphosphates such as sodium tripolyphosphate and potassium tripolyphosphate.

The pyrophosphate salts are incorporated in a dentifrice component of the present invention at a concentration of about 0.05 to about 2.0% by weight, and preferably about 0.5 to about 2% by weight. Polyphosphate salts can be incorporated in the dentifrice composition of the present invention at a concentration of about 1.0 to about 7.0% by weight.

Colorants such as pigments and dyes may be used in the practice of the present invention. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium slat of 4-{[4-(N-ethyl-p-sulffobenzylamino)-phenyl]-(4-hydroxy-2-sulfoniumphenyl)-mewthylene}-[1-(N-ethyl-N-p-sulfobenzyl)-Δ-3,5-cyclohexadienimine], FD&C Blue No. 1 (disodium salt of dibenzyldiethyldiaminotriphenylcarbinol trisulfonic acid of indigotin) and mixtures thereof in various proportions. The concentration of the dye for the most effective result in the present invention is present in the dentifrice composition in an amount from about 0.0005 percent to about 2 percent of the total weight.

A striped dentifrice product may be obtained using the dual component dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both the pigments and dyes discussed above.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.01% to 5% or more of the preparations.

To prepare either of the dentifrice components of the present invention, generally the humectants e.g. glycerin, propylene glycol, polyethylene glycol are used to disperse with any organic thickeners, pigments such as titanium dioxide and any polyphosphates included as anti-calculus ingredients. Water is then added into this dispersion followed by sweetener. In the first component, the zinc and chlorite salts as well as a fluoride ion source is added. In the second component an ingredient to lower the pH to an acid level is added, such as phosphoric acid. These ingredients are mixed until a homogenous phase is obtained for each component. Thereafter inorganic thickener, silica abrasive, flavor and surfactant ingredients are added and the ingredients mixed at high speed under vacuum of from about 20 to 100 mm of Hg. The resultant product in the case of each component is a homogeneous, semi-solid, extrudible paste product.

The multicomponent dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a tube, having collapsible sidewalls, as disclosed in U.S. Pat. Nos. 4,487,757, 4,687,663 and 5,954,234; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following Examples are further illustrative of the present invention, but it is understood that the invention is not limited thereto. All amounts and proportions referred to herein and in the appended claims are by weight, unless otherwise stated.

EXAMPLE I

A two component (Component 1 and 2) dentifrice of the present invention was prepared, designated Composition A, Component 1 having a substantially neutral pH and Component 2 having an acid pH. The ingredients and pH of Components 1 and 2 of Composition A are listed in Table I, below. Components 1 and 2 when combined had a pH of 6.4.

TABLE I

| COMPOSITION A | | |
|---|---|---|
| Component Ingredients | 1 Weight % | 2 Weight % |
| Polyethylene glycol | 3.000 | 3.000 |
| Sodium carboxymethyl cellulose | 0.600 | 0.600 |
| Sorbitol | 57.608 | 57.699 |
| Titanium dioxide | 0.500 | 0.500 |
| Water | q.s. | q.s. |

TABLE I-continued

| COMPOSITION A | | |
|---|---|---|
| Component Ingredients | 1 Weight % | 2 Weight % |
| Sodium fluoride | 0.243 | 0.243 |
| Sodium saccharin | 0.300 | 0.300 |
| Silica | 25.500 | 25.500 |
| Flavor | 1.000 | 1.000 |
| Sodium lauryl sulfate | 1.200 | 1.200 |
| Zinc nitrate hexahydrate | 0.911 | — |
| Sodium chlorite | 0.550 | — |
| Phosphoric acid (75% solution) | — | 0.700 |
| FD&C Blue No. 1 (1% solution) | — | 0.138 |
| Total | 100.000 | 100.00 |
| pH | 6.45 | 4.5 |

Composition A was packaged in a dual chambered tube which when squeezed delivered substantially equal volumes of Components 1 and 2.

A human study was conducted to compare the 5 hour effect of Composition A on the volatile sulfur compounds (VSC) responsible for mouth odor. VSC levels were measured using a Halimeter™ (Model # RH17E), a commercially available sulfide monitor, using breath sample drawn from the subjects mouth through a straw (6 mm) directly into the sample port detector. A VSC level above 180 parts per billion (ppb) is considered to result in offensive mouth odor.

Five subjects were involved in a randomized, double blind study design with a cross over phase. After an initial morning baseline evaluation, and breakfast, subjects brushed with an assigned dentifrice composition for 1 minute. After the subjects used the assigned dentifrice, they were asked to return to the study site 5 hours later for post treatment evaluation. After a 1 day washout period between each treatment product, the subjects repeated the same treatment procedure with a newly assigned product during the cross over phase. Each subject used each of 3 Compositions, designated A and B and C. During the washout period, subjects used a regular commercial fluoride dentifrice.

Composition A was the dual component dentifrice of Table I.

Composition B was a clinically proven single component, commercially available breath freshening dentifrice which contained the antibacterial agent Triclosan which was used as a positive control.

Composition C was a commercially available fluoride (NaF) dentifrice used as a negative control.

The VSC levels observed in the study are recorded in Table II below.

TABLE II

| VSC LEVELS (ppb) | | | |
|---|---|---|---|
| Composition | Baseline Mean | Final Mean | % VSC Reduction |
| A | 348 | 157 | 55 |
| B | 312 | 163 | 48 |
| C | 328 | 245 | 28 |

The results recorded in Table II indicate that Composition A, was more effective than Composition B in reducing VSC levels when compared to the negative control dentifrice (Composition C) and had reduced the VSC level substantially below the offensive level of 180 ppb.

EXAMPLE II

The procedure of Example I was repeated except an additional comparative dentifrice designated "Composition D" was evaluated for VSC level reduction. Composition D was prepared with the same ingredients as Composition A except zinc nitrate and phosphoric acid were not included as ingredients in Component 1 and 2 respectively.

The VSC levels observed in the study are recorded in Table III below.

TABLE III

VSC LEVELS (ppb)

| Composition | Baseline Mean | Final* Mean | % VSC Reduction |
|---|---|---|---|
| A | 412 | 159 | 61 |
| B | 349 | 209 | 40 |
| C | 329 | 310 | 6 |
| D | 363 | 229 | 37 |

The results recorded in Table III show that Composition A containing both chlorite +zinc ions was also more effective than Composition D which did not contain zinc ion. The results indicate that the presence of zinc ion and the in situ generated chlorine dioxide generated by the intermixing of Component 1 with an acidulated Component 2 boosted the efficacy of the dentifrice composition of the present invention as compared to the dentifrice composition with only sodium chlorite and the absence of an acidulated second component.

What is claimed is:

1. A method to suppress oral malodor and provide long lasting fresh breath in the oral cavity comprising applying to the oral cavity a dual component oral composition which comprises a first dentifrice component having a substantially neutral pH and containing a zinc ion releasable compound and a chlorite ion releasable compound, the second dentifrice component having an acid pH, the first and second components being maintained separate from each other until dispensed and combined for application to teeth, the combined components having a pH of no greater than 7.

2. The method of claim 1 wherein the zinc ion releasable compound is zinc nitrate.

3. The method of claim 1 wherein the chlorite ion releasable compound is sodium chlorite.

4. The method of claim 1 wherein the first dentifrice component is an aqueous dentifrice having a pH of about 6.0 to about 7.5.

5. The method of claim 1 wherein the second dentifrice component has a pH of about 2 to about 6.

6. The method of claim 1 wherein the pH of the acidic dentifrice component is adjusted with phosphoric acid.

7. The method of claim 1 wherein the zinc ion releasable compound is present in the first dentifrice component at a concentration of about 0.25% to about 10% by weight.

8. The method of claim 1 wherein the chlorite ion releasable compound is present in the first dentifrice component at a concentration of about 0.05% to about 5% by weight.

9. A dual component oral composition to suppress oral malodor and provide long lasting breath protection in the oral cavity which comprises a first dentifrice component having a substantially neutral pH and containing a zinc ion releasable compound and a chlorite ion releasable compound, the second dentifrice component having an acid pH, the first and second components being maintained separate from each other until dispensed and combined for application to teeth.

10. The composition of claim 9 wherein the zinc ion releasable compound is zinc nitrate.

11. The composition of claim 9 wherein the chlorite ion releasable compound is sodium chlorite.

12. The composition of claim 9 wherein the first dentifrice component is an aqueous dentifrice having a pH of about 6.0 to about 7.5.

13. The composition of claim 1 wherein the second dentifrice component has a pH of about 2 to about 6.

14. The composition of claim 9 wherein the pH of the acidic dentifrice component is adjusted with phosphoric acid.

15. The composition of claim 9 wherein the zinc ion releasable compound is present in the first dentifrice component at a concentration of about 0.25 to about 10% by weight.

16. The composition of claim 9 wherein the chlorite ion releasable compound is present in the first dentifrice component at a concentration of about 0.05% to abut 5% by weight.

* * * * *